United States Patent [19]

Chang et al.

[11] Patent Number: 5,543,036
[45] Date of Patent: Aug. 6, 1996

[54] PROCESS FOR HYDROTREATING

[75] Inventors: Clarence D. Chang, Princeton; Scott Han, Lawrenceville, both of N.J.; Daniel J. Martenak, Dublin, Pa.; Jose G. Santiesteban, Yardley, Pa.; Dennis E. Walsh, Richboro, Pa.

[73] Assignee: Mobil Oil Corporation, Fairfax, Va.

[21] Appl. No.: 167,108

[22] Filed: Dec. 16, 1993

Related U.S. Application Data

[63] Continuation-in-part of Ser. No. 95,884, Jul. 22, 1993.

[51] Int. Cl.$^6$ .............. C10G 17/00; C10G 17/095; C10G 45/04
[52] U.S. Cl. .............. 208/189; 208/208 R; 208/209; 208/213; 208/214; 208/216 R; 208/217; 208/251 H; 208/254 H
[58] Field of Search .............. 208/189, 208 R, 208/209, 213, 214, 216 R, 217, 251 H, 254 H

[56] References Cited

U.S. PATENT DOCUMENTS

| | | | |
|---|---|---|---|
| 3,393,149 | 7/1968 | Conley et al. | 210/42 |
| 3,674,680 | 7/1972 | Hoekstra et al. | 208/111 |
| 3,730,879 | 5/1973 | Christman et al. | 208/210 |
| 3,764,565 | 10/1973 | Jacobs et al. | 252/470 |
| 3,814,683 | 6/1974 | Christman et al. | 208/216 |
| 3,841,995 | 10/1974 | Bertolacini et al. | 208/89 |
| 3,873,470 | 3/1975 | Conway et al. | 205/216 |
| 3,876,523 | 4/1975 | Rosinski et al. | 208/89 |
| 3,882,049 | 5/1975 | Bertolacini et al. | 252/466 PT |
| 3,902,991 | 9/1975 | Christensen et al. | 208/211 |
| 3,909,450 | 9/1975 | O'Hara | 208/216 |
| 3,998,721 | 12/1976 | O'Hara | 208/111 |
| 4,016,067 | 4/1977 | Fischer et al. | 208/89 |
| 4,032,435 | 6/1977 | Schmitt, Jr. et al. | 208/216 |
| 4,051,021 | 9/1977 | Hamner | 208/216 |
| 4,069,139 | 1/1978 | Riley et al. | 208/216 |
| 4,073,718 | 2/1978 | Hamner | 208/80 |
| 4,783,575 | 11/1988 | Schmidt et al. | 585/748 |
| 4,861,746 | 8/1989 | Oishi et al. | 208/251 H |
| 4,918,041 | 4/1990 | Hollstein et al. | 502/217 |
| 5,008,003 | 4/1991 | Smegal et al. | 208/251 H |
| 5,113,034 | 5/1992 | Soled et al. | 585/510 |

FOREIGN PATENT DOCUMENTS 1288339  11/1989  Japan.

OTHER PUBLICATIONS

*Proceedings 9th International Congress on Catalysis*, vol. 4, 1727–1735 (1988), K. Arata and M. Hino *no month available.

Hino and Arata, "Synthesis of Solid Superacid of Tungsten Oxide Supported on Zirconia and Its Catalytic Action for Reactions of Butane and Pentane", J. Chem. Soc., Chem. Commun., 1259–1260 (1988) *no month available.

*Primary Examiner*—E. Rollins Cross
*Assistant Examiner*—E. D. Irzinski
*Attorney, Agent, or Firm*—Ronald A. Bleeker; Dennis P. Santini; Lori F. Cuomo

[57] ABSTRACT

A process for hydrotreating a hydrocarbon feedstock, such as light cycle oil, using a catalyst composition containing a hydrogenation/dehydrogenation component and an acidic solid component including a Group IVB metal oxide modified with an oxyanion of a Group VIB metal. The hydrotreating process removes contaminants, such as sulfur and/or nitrogen, from the feedstock.

20 Claims, No Drawings

PROCESS FOR HYDROTREATING

CROSS-REFERENCE TO RELATED APPLICATIONS

This application is a continuation-in-part of co-pending application Ser. No. 08/095,884 filed Jul. 22, 1993, entitled "Paraffin Isomerization Catalyst and Process for Its Use" incorporated herein in its entirety by reference. This application is further related by subject matter to co-pending application Ser. No. 08/150,304 filed Nov. 10, 1993, entitled "A Process for Selective Wax Hydrocracking" and copending application Ser. No. 08/150,303 filed Nov. 10, 1993, entitled "A Process for Naphtha Hydrocracking".

FIELD OF THE INVENTION

The process of the present invention relates to a process for hydrotreating a hydrocarbon feedstock using a catalyst comprising an acidic solid component comprising a Group IVB metal oxide modified with an oxyanion of a Group VIB metal.

BACKGROUND

The use of hydrotreating (HDT) to upgrade hydrocarbon fractions for use as charge stocks for catalytic cracking, for example, was well known by the 1960's. Hydrotreating, as used herein, is meant to encompass those processes using hydrogen in the presence of catalysts in order to remove undesirable compounds from hydrocarbons, that is to upgrade the hydrocarbons. In hydrocracking, however, a substantial amount of the feed is converted to lower boiling range products, i.e. there is a significant change in the boiling range of the products versus the feed.

By 1960, it was recognized that hydrotreatment could be used for demetalation, desulfurization, Conradson Carbon Residue reduction and denitrogenation. There was universal recognition at that time in the art that hydrogenation catalysts comprising Group VI (Cr, Mo, W) and Group VIII metals or their oxides or sulfides deposited on porous refractory supports were extremely useful in hydrotreating processes. Preferred catalysts for hydrotreating were considered to be cobalt-molybdate or nickel-molybdate supported on alumina. These catalysts are generally referred to as "conventional HDT catalysts."

The pore size distribution of the HDT catalyst is a very important parameter in determination of the activity of the catalyst. Large pore catalysts generally possess greater demetalating activity and smaller pore catalysts generally possess lower demetalation activity, but higher desulfurization activity. U.S. Pat. No. 3,730,879 teaches an HDT process comprising a multi-layered arrangement of catalyst with different pore distributions. In the first bed, there is used a smaller pore catalyst which is more selective for desulfurization; and in the second downstream bed, there is used a larger pore catalyst which is more selective for removal of metal contaminants. According to U.S. Pat. No. 3,730,879, the desulfurization catalyst of the first bed has a catalyst characterized by a pore diameter distribution as follows: less than 25% 0–100 Å; greater than 50% 100–200 Å; and the remainder 200–600 Å. The demetalation catalyst of the second bed has a catalyst characterized by a pore diameter distribution as follows: less than 20% 0–100 Å; less than 45% 100–200 Å; and balance 200–600 Å.

The average pore diameter size for HDT catalysts in desulfurization processes is usually 100–200 Å. Such average pore diameter size is disclosed in U.S. Pat. Nos. 3,393,148; 3,674,680; 3,764,565; 3,841,995 and 3,882,049.

Processes for the demetalation and desulfurization of oil fractions using conventional HDT catalysts with at least 60% of its pore volume in pores of 100 Å to 200 Å diameter and at least 5% of its pore volume in pores having diameters greater than 500 Å are disclosed in U.S. Pat. Nos. 3,876,523 and 4,016,067.

U.S. Pat. No. 3,902,991 discloses a hydrodesulfurization process for oil fractions which uses a conventional HDT catalyst having at least 50% of its total pore volume in pores having a diameter size range of 65 to 150 Å. Another hydrodesulfurization process for oil fractions is described in U.S. Pat. No. 3,730,879, wherein one of the catalysts has at least 50% of its total pore volume in pores having radii in the size range of 50–100 Å. Still another hydrodesulfurization process is disclosed in U.S. Pat. No. 3,814,683. In this patent, the conventional HDT catalyst is characterized by having at least 65% of its total pore volume in pores having a diameter size of 80–180 Å.

Other hydrodesulfurization processes using a conventional HDT catalyst having a specific pore size distribution are disclosed in U.S. Pat. Nos. 4,032,435; 4,051,021; 4,069,139 and 4,073,718.

It has now been found that a solid acid catalyst comprising a Group IVB metal oxide modified with an oxyanion of a Group VIB metal may be employed as the basis for hydrotreating catalysts used to upgrade a hydrocarbon feedstock. Preferably, a hydrogenation component is incorporated in the hydrotreating catalyst. The catalyst enhances removal of undesirable metals, sulfur, nitrogen and Conradson carbon residue.

SUMMARY OF THE INVENTION

There is described herein a catalytic process for hydrotreating a hydrocarbon feedstock, such as a light cycle oil. Processing a hydrocarbon feed over a catalyst comprising a Group IVB metal oxide modified with an oxyanion of a Group VIB metal results in significant desulfurization and denitrogenation. The feedstock may be hydrotreated under mild or moderate hydroprocessing conditions to reduce sulfur, nitrogen, oxygen and metal content in the feedstock.

The invention therefore includes a process for hydrotreating a hydrocarbon feedstock comprising contacting said hydrocarbon feedstock under hydrotreating conditions with hydrogen in the presence of a catalyst comprising a hydrogenation/dehydrogenation component and an acidic solid component comprising a Group IVB metal oxide modified with an oxyanion of a Group VIB metal.

DETAILED DESCRIPTION OF THE INVENTION

A hydrocarbon feedstock is contacted under hydrotreating conditions with the catalyst of the present invention to produce a product having reduced sulfur and/or nitrogen content. The hydrotreating process may be applied to a wide range of feedstocks from naphtha to reduced crude.

The process of the present invention is applicable to any sulfur and/or nitrogen containing feedstock. Feeds suitable for use in the hydrotreating step of the present invention include, but are not limited to, crude petroleum, reduced crudes, cycle oils, vacuum tower residua, vacuum gas oils, deasphalted residua and other heavy oils, fuel oils and slack waxes.

The catalyst used in the process of the present invention comprises an oxide of a Group IVB metal, preferably zirconia or titania. This Group IVB metal oxide is modified in two ways. According to one modification, the Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceedings 9th International Congress on Catalysis*, 4, 1727–1735 (1988), the entire disclosures of these publications are expressly incorporated herein by reference.

According to another modification of the Group IVB metal oxide described herein, a hydrogenation/dehydrogenation component is combined with the Group IV metal oxide. This hydrogenation/dehydrogenation component imparts the ability of the material to catalyze the addition of hydrogen to or the removal of hydrogen from organic compounds, such as hydrocarbons, optionally substituted with one or more heteroatoms, such as oxygen, nitrogen, metals or sulfur, when the organic compounds are contacted with the modified material under sufficient hydrogenation or dehydrogenation conditions.

Examples of hydrogenation/dehydrogenation components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi), Group VIB metals (i.e., Mo), and Group VIIB metals (i.e., Mn, Tc and Re). The present catalyst may comprise one or more catalytic forms of one or more noble metals (i.e., Pt, Pd, Ir, Rh, Os or Ru). Combinations of catalytic forms of such noble or non-noble metals, such as combinations of Pt with Sn, may be used. The valence state of the metal of the hydrogenation/dehydrogenation component is preferably in a reduced valance state, e.g., when this component is in the form of an oxide or hydroxide. The reduced valence state of this metal may be attained, in situ, during the course of a reaction, when a reducing agent, such as hydrogen, is included in the feed to the reaction.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

This chemical interaction is discussed in the aforementioned article by K. Arata and M. Hino in *Proceedings 9th International Congress on Catalysis*, 4, 1727–1735 (1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Other elements, such as alkali (Group IA) or alkaline earth (Group IIA) compounds may optionally be added to the present catalyst to alter catalytic properties. The addition of such alkali or alkaline earth compounds to the present catalyst may enhance the catalytic properties of components thereof, e.g., Pt or W, in terms of their ability to function as a hydrogenation/dehydrogenation component or an acid component.

The Group IVB metal (i.e., Ti, Zr or Hf) and the Group VIB metal (i.e., Cr, Mo or W) species of the present catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic ability of the catalyst to catalyze certain reactions, e.g., the hydrocracking of waxy feeds.

Suitable sources of the Group IVB metal oxide, used for preparing the present catalyst, include compounds capable of generating such oxides, such as oxychlorides, chlorides, nitrates, etc., particularly of zirconium or titanium. Alkoxides of such metals may also be used as precursors or sources of the Group IVB metal oxide. Examples of such alkoxides include zirconium n-propoxide and titanium ipropoxide. Preferred sources of a Group IVB metal oxide are zirconium hydroxide, i.e., $Zr(OH)_4$, and hydrated zirconia. The expression, hydrated zirconia, is intended to connote materials comprising zirconium atoms covalently linked to other zirconium atoms via bridging oxygen atoms, i.e., Zr-O-Zr, further comprising available surface hydroxy groups. These available surface hydroxyl groups are believed to react with the source of an anion of a Group IVB metal, such as tungsten, to form the present acidic catalyst component. As suggested in the afformentioned article by K. Arata and M. Hino in *Proceedings 9th International Congress on Catalysis*, 4, 1727–1735 (1988), precalcination of $Zr(OH)_4$ at a temperature of from about 100° C. to about 400° C. results in a species which interacts more favorably with tungstate. This precalcination is believed to result in the condensation of ZrOH groups to form a polymeric zirconia species with surface hydroxyl groups. This polymeric species is referred to herein as a form of a hydrated zirconia.

Treatment of hydrated zirconia with a base solution prior to contact with a source of tungstate may be preferable. More particularly, as demonstrated in Examples recited hereinafter, especially in Examples 16–25, refluxing hydrated zirconia in an $NH_4OH$ solution having a pH of greater than 7 was beneficial. Without wishing to be bound by any theory, it is theorized that the base-treated, hydrated zirconia is better because it has higher surface area. It is also theoretically possible that the base treatment alters surface hydroxyl groups on the hydrated zirconia, possibly in a manner which promotes a more desirable interaction with the source of tungstate later used.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate.

The hydrogenation/dehydrogenation component of the present catalyst may be derived from Group VIII metals, such as platinum, iridium, osmium, palladium, rhodium, ruthenium, nickel, cobalt, iron and mixtures of two or more thereof. These components may optionally be mixed with components derived from Group IVA metals, preferably Sn, and/or components derived from Group VIIB metals, preferably rhenium and manganese. These components may be added to the catalyst by methods known in the art, such as ion exchange, impregnation or physical admixture. For example, salt solutions of these metals may be contacted with the remaining catalyst components under conditions sufficient to combine the respective components. The metal containing salt is preferably water soluble. Examples of such salts include chloroplatinic acid, tetraammineplatinum complexes, platinum chloride, tin sulfate and tin chloride.

The present catalyst may be prepared, for example, by impregnating the hydroxide or oxide, particularly the hydrated oxide, of the Group IVB metal with an aqueous solution containing an anion of the Group VIB metal, preferably tungstate or molybdate, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.5–24 hours, and more preferably for about 1.0–10 hours. In a most preferred embodiment, calcination is carried out at about 800° C. for about 1 to about 3 hours. The hydrogenation/dehydrogenation component of the catalyst (e.g., Group VIII metal, Group VIIB metal, etc.) may be added after or before the calcination step by techniques known in the art, such as impregnation, coimpregnation, coprecipitation, physical admixture, etc. The hydrogenation/dehydrogenation component may also be combined with the remaining catalyst components before or after these remaining components are combined with a binder or matrix material as described hereinafter.

When a source of the hydroxide or hydrated oxide of zirconium is used, calcination, e.g., at temperatures greater than 500° C., of the combination of this material with a source of an oxyanion of tungsten may be needed to induce the theorized chemical reaction which imparts the desired degree of acidity to the overall material. However, when more reactive sources of zirconia are used, it is possible that such high calcination temperatures may not be needed.

In the present catalyst, of the Group IVB oxides, zirconium oxide is preferred; of the Group VIB anions, tungstate is preferred; and of the hydrogenation/ dehydrogenation components, platinum and/or platinum-tin are preferred.

Qualitatively speaking, elemental analysis of the present catalyst will reveal the presence of Group IVB metal, Group VIB metal and oxygen. The amount of oxygen measured in such an analysis will depend on a number of factors, such as the valence state of the Group IVB and Group VIB metals, the form of the hydrogenation/dehydrogenation component, moisture content, etc. Accordingly, in characterizing the composition of the present catalyst, it is best not to be restricted by any particular quantities of oxygen. In functional terms, the amount of Group VIB oxyanion in the present catalyst may be expressed as that amount which increases the acidity of the Group IVB oxide. This amount is referred to herein as an acidity increasing amount. Elemental analysis of the present catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form of $YO_3$. It will be appreciated, however, that these forms of oxides, i.e., $XO_2$ and $YO_3$, may not actually exist, and are referred to herein simply for the purposes of calculating relative quantities of X and Y in the present catalyst. The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30.

The amount of hydrogenation/dehydrogenation component may be that amount which imparts or increases the catalytic ability of the overall material to catalytically hydrogenate or dehydrogenate a hydrogenatable or dehydrogenatable organic compound under sufficient hydrogenation or dehydrogenation conditions. This amount is referred to herein as a catalytic amount. Quantitatively speaking, the present catalyst may comprise, for example, from about 0.001 to about 5 wt %. e.g., from about 0.1 to about 2 wt % of the hydrogenation/dehydrogenation component, especially when this component is a noble metal.

It may be desirable to incorporate the present catalyst with another material to improve its properties. Such materials include active and inactive materials and synthetic or naturally occurring zeolites as well as inorganic materials such as clays, silica, and/or metal oxides. The latter may be either naturally occurring or in the form of gelatinous precipitates, sols, or gels including mixtures of silica and metal oxides.

The present catalyst includes a hydrogenation-dehydrogenation component to the catalyst. Metals having a strong hydrogenation function are preferred, especially platinum and the other noble metals such as palladium, rhodium, iridium, rhenium, although other metals capable of acting as a hydrogenation component may also be used, for example, nickel, tungsten or other metals of Group VIIIA of the Periodic Table (IUPAC Table), either singly, in mixtures or in combination with other metals. The amount of the noble metal component may be in the range 0.001 to 5 wt. % of the total catalyst, e.g., from 0.1 to 2 wt. %. Base metal hydrogenation components may be added in somewhat greater amounts. The hydrogenation component can be exchanged onto the support material, impregnated into it or physically admixed with it. If the metal is to be impregnated into or exchanged onto the support, it may be done, for example, by treating the support with a platinum metal-containing ion. Suitable platinum compounds include chloroplatinic acid, platinous chloride and various compounds containing the platinum ammine complex. The metal compounds may be either compounds in which the metal is present in the cation or anion of the compound; both types of compounds can be used. Platinum compounds in which the metal is in the form of a cation of cationic complex, e.g., $Pt(NH_3)_4Cl_2$ are particularly useful, as are anionic complexes such as the vanadate and metatungstate ions. Cationic forms of other metals are also useful since they may be exchanged onto the support or impregnated into it.

The catalyst may be subjected to a final calcination under conventional conditions in order to convert the metal component to the oxide form and to confer the required mechanical strength on the catalyst. Prior to use, the catalyst may be subjected to presulfiding.

When a source of hydrogenation metal, such as $H_2PtCl_6$, is used as a source of a hydrogenation-dehydrogenation component in the present catalyst, it may be desirable to subject the present catalyst to extended reducing conditions, e.g., lasting more than 4 hours.

The present catalyst can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the catalyst can be extruded before drying or partially dried and then extruded. The present catalyst may be composited with a matrix material to form the finished form of the catalyst and for this purpose conventional matrix materials such as alumina, silica-alumina and silica are suitable with preference given to silica as a non-acidic binder. Other binder materials may be used, for example, titania, zirconia and other metal oxides or clays. The active catalyst may be composited with the matrix in amounts from 80:20 to 20:80 by weight, e.g., from 80:20 to 50:50 active catalyst:matrix. Compositing may be done by conventional means including mulling the materials together followed by extrusion of pelletizing into the desired finished catalyst particles.

The catalyst may be treated by conventional pre-sulfiding treatments, e.g., by heating in the presence of hydrogen sulfide, to convert oxide forms of the metal components to their corresponding sulfides. The catalyst may also be treated with gases, such as $H_2$ and $N_2$, at elevated temperatures prior to contacting with feed to improve catalyst activity.

The process of the present invention may be carried out by contacting a sulfur and/or nitrogen contaminated feedstock with the above described hydrotreating catalyst in the presence of hydrogen at pressures in the range of from about 200 to about 3000 psig; temperatures in the range of from about 200° to about 1000° F.; liquid hourly space velocities (LHSV) in the range of from about 0.1 to about 10.0 $hr^{-1}$; and hydrogen:feedstock ratios (hydrogen circulation rates) in the range of from about 400 to about 5000 SCF/Bbl $H_2$. For hydrodesulfurization, preferably theses conditions include a pressure in the range of from about 250 to about 500 psig, a temperature in the range of from about 500° to about 700° F., a liquid hourly space velocity in the range of from about 0.1 to about 2.0 $hr^{-1}$ and a hydrogen:feedstock ratio (hydrogen circulation rate) in the range of from about 400 to about 2000 SCF/Bbl $H_2$. For denitrogenation, preferably these conditions include pressures in the range of from about 600 to about 2000 psig; temperatures in the range of from about 500° to about 750° F.; liquid hourly space velocities in the range of from about 0.1 to about 2.0 $hr^{-1}$; and hydrogen:feedstock ratios (hydrogen circulation rates) in the range of from about 500 to about 3000 SCF/Bbl $H_2$. Generally, the hydrotreatment process of the present invention results in less than or equal to about 20% conversion to gasoline.

The catalytic hydrotreating may take place in any suitable hydrotreating reactor, preferably a fixed bed downflow (trickle bed) reactor. Other suitable hydrotreaters include moving bed downflow ("bunker") reactors, fluidized bed or ebullated bed raectors and fixed bed upflow reactors.

The following example illustrates the hydrotreating process of the present invention.

EXAMPLE

The tungsten oxide/zirconia catalyst was prepared by impregnating 15 wt. % tungsten as ammonium metatungstate on dry $Zr(OH)_4$. The hydrous zirconia was prepared by dissolving $ZrOCl_2$ in water, precipitating out with $NH_4OH$, and subsequent overnight refluxing of the precipitate in water set to pH~9 with $NH_4OH$. After tungsten impregnation, the catalyst was calcined at 825° C. in air for 4 hours. Hexachloroplatinic acid was impregnated on the tungsten/zirconia catalyst (target 0.5 wt. % Pt) and the resultant mixture calcined at 300° C. in air for 2 hours.

The finished catalyst was pelleted and sized at 24/40 mesh. Ten cc. of catalyst was diluted with sand in a 1;1 ratio and charged to a ½" i.d. microreactor. The catalyst was reduced prior to running by flowing $H_2$ (300 cc/min) at 300° C. for 90 hours. After a standard sulfiding with $H_2S$, the catalyst was contacted with a light cycle oil feed having the following properties as set forth in Table 1.

TABLE 1

| | |
|---|---|
| Carbon, wt % | 87.04 |
| Hydrogen, wt % | 9.97 |
| Nitrogen, wt % | 0.04 |
| Sulfur, wt % | 2.95 |
| Boiling Range, wt % | |
| $C_6$-330° F. | 2.0 |
| 330–420° F. | 7.0 |
| 420–650° F. | 75.5 |
| 650° F. | 15.5 |

Three runs were conducted. The conditions for each run are given in Table 2 below. The data in Table 2 shows the catalyst of the present invention is effective for hydrodesulfurization (HDS) and hydrodenitrogenation (HDN). The catalyst showed significant HDS and HDN activity with greater than about 90% heteroatom removal.

TABLE 2

| | Run No. | | |
|---|---|---|---|
| | 1 | 2 | 3 |
| Temp., °F. | 675 | 700 | 725 |
| LHSV, $hr^{-1}$ | 1.0 | 1.0 | 0.7 |
| $H_2$ circulation, SCF/Bbl | 3050 | 3790 | 4430 |
| Pressure, psig | 1900 | 1900 | 1900 |
| Product Yields, wt % | | | |
| $H_2S$ | No data | 1.9 | 2.0 |
| $C_1 + C_2$ | 0.2 | 0.2 | 0.3 |
| $C_3 + C_4$ | 0.1 | 0.2 | 0.3 |
| $C_5$'s | 0.4 | 0.0 | 0.0 |
| $C_6$-330° F. | 4.2 | 3.6 | 5.8 |
| 330–420° F. | 13.7 | 11.5 | 15.0 |
| 420–650° F. | 72.6 | 75.9 | 71.0 |
| 650° F.$^+$ | 8.8 | 6.7 | 5.6 |
| Net Conversion to: | | | |
| 420° F.- Products | 10.5 | 9.2 | 15.8 |
| % HDS | No data* | 93 | >99 |
| % HDN | 98 | >99 | >99 |
| Wt % Total Products as $C_6^+$ Liquids | 99.3 | 97.7 | 97.4 |
| Wt % Hydrogen in Liquid Products | 11.77 | 11.98 | 12.48 |
| $H_2$ Consumption, SCF/Bbl | 1074 | 1120 | 1410 |
| % Hydrogen Consumption for: | | | |

TABLE 2-continued

| | Run No. | | |
|---|---|---|---|
| | 1 | 2 | 3 |
| HDN/HDS | No data | ~9 | ~8 |
| Enriched Liquid Products | ≧90 | ~90 | ~90 |

*Analytical Failure

Changes and modifications in the specifically described embodiments can be carried out without departing from the scope of the invention which is intended to be limited only by the scope of the appended claims.

What is claimed is:

1. A process for hydrotreating a hydrocarbon feedstock comprising contacting said hydrocarbon feedstock under hydrotreating conditions with hydrogen in the presence of a catalyst comprising a hydrogenation/dehydrogenation catalytic component and an acidic solid catalytic component comprising a Group IVB metal oxide modified with an oxyanion of a Group VIB metal, wherein said Group IVB metal oxide consists essentially of a hydrated zirconia.

2. A process according to claim 1, wherein said hydrogenation/dehydrogen component comprises at least one metal in the form of at least one oxide, hydroxide or free metal of at least one element selected from the group consisting of Group VIII metals, Group IVA metals, Group VB metals, Group VIB metals and Group VIIB metals.

3. A process according to claim 2, wherein said hydrogenation/dehydrogenation component further comprises a noble metal.

4. A process according to claim 1, wherein said hydrogenation/dehydrogenation component comprises a noble metal.

5. A process according to claim 1, wherein said hydrogenation/dehydrogenation component comprises platinum.

6. A process according to claim 2, wherein said hydrogenation/dehydrogenation component further comprises tin.

7. A process according to claim 1, wherein said Group VIB metal oxyanion is an oxyanion of molybdenum or tungsten.

8. A process according to claim 1, wherein said hydrogenation/dehydrogenation component comprises platinum in the form of an oxide, hydroxide or free metal and said Group VIB metal oxyanion is tungstate.

9. A process according to claim 1, wherein said catalyst comprises a calculated mole ratio of $XO_2/YO_3$, where X is the Group IVB metal and Y is said Group VIB metal, of up to 300 and from 0.001 wt. % to about 5 wt. % of said hydrogenation/dehydrogenation component, based upon the total weight of the catalyst.

10. A process according to claim 8, wherein said catalyst comprises a calculated mole ratio of $XO_2/YO_3$, where X is the Group IVB metal and Y is said Group VIB metal, of from 2 to 100 and from 0.001 wt. % to about 5 wt. % of said hydrogenation/dehydrogenation component, based upon the total weight of the catalyst.

11. A process according to claim 8, wherein said catalyst comprises a calculated mole ratio of $XO_2/YO_3$, where X is the Group IVB metal and Y is said Group VIB metal, of from 4 to 30 and from 0.1 wt. % to about 2 wt. % of platinum, based upon the total weight of the catalyst.

12. A process according to claim 1 wherein said hydrocarbon feedstock is a light cycle oil.

13. A process according to claim 1 wherein greater than about 90% sulfur is removed from said hydrocarbon feedstock.

14. A process according to claim 1 wherein greater than about 90% nitrogen is removed from said hydrocarbon feedstock.

15. A process according to claim 1 wherein said contacting results in less than or equal to about 20% conversion of said hydrocarbon feedstock to gasoline.

16. A process according to claim 1 wherein said hydrotreating conditions include a pressure in the range of from about 200° to about 3000 psig; a temperature in the range of from about 200° to about 1000° F.; a liquid hourly space velocity in the range of from about 0.1 to about 10.0 $hr^1$; and a hydrogen:feedstock ratio in the range of from about 400 to about 5000 SCF/Bbl $H_2$.

17. A process according to claim 1 wherein said hydrotreating conditions include a pressure in the range of from about 250 to about 500 psig; a temperature in the range of from about 500° to about 700° F.; a liquid hourly space velocity in the range of from about 0.1 to about 2.0 $hr^1$; and a hydrogen:feedstock ratio in the range of from about 400 to about 2000 SCF/Bbl $H_2$.

18. A process according to claim 1 wherein said hydrotreating conditions include a pressure in the range of from about 600 to about 2000 psig; a temperature in the range of from about 500° to about 750° F.; a liquid hourly space velocity in the range of from about 0.1 to about 2.0 $hr^1$; and a hydrogen:feedstock ratio in the range of from about 500 to about 3000 SCF/Bbl $H_2$.

19. A process according to claim 1, wherein said Group IVB metal oxide is modified with an acidity increasing amount of said oxyanion of a Group VIB metal.

20. A process according to claim 1, wherein said catalyst is prepared by calcining at a temperature in the range of from about 700° C. to about 900° C.

* * * * *